(12) United States Patent
Sitkovsky

(10) Patent No.: US 7,718,624 B2
(45) Date of Patent: May 18, 2010

(54) MODULATION OF IMMUNE RESPONSE AND INFLAMMATION BY TARGETING HYPOXIA INDUCIBLE FACTORS

(76) Inventor: Michail V. Sitkovsky, 85 E. India Row #2 B, Boston, MA (US) 02110

( * ) Notice: Subject to any disclaimer, the term of this patent is extended or adjusted under 35 U.S.C. 154(b) by 117 days.

(21) Appl. No.: 11/215,224

(22) Filed: Aug. 29, 2005

(65) Prior Publication Data
US 2007/0249550 A1 Oct. 25, 2007

Related U.S. Application Data

(60) Provisional application No. 60/606,449, filed on Sep. 1, 2004.

(51) Int. Cl.
*A61K 31/70* (2006.01)
*C07H 21/04* (2006.01)
(52) U.S. Cl. .................. 514/44; 536/23.1; 536/24.5
(58) Field of Classification Search .................. None
See application file for complete search history.

(56) References Cited

U.S. PATENT DOCUMENTS

| 6,670,334 | B2* | 12/2003 | Linden et al. ............ 514/46 |
| 2003/0143732 | A1* | 7/2003 | Fosnaugh et al. ........ 435/325 |
| 2003/0170891 | A1* | 9/2003 | McSwiggen ............. 435/366 |
| 2004/0101858 | A1* | 5/2004 | Ward et al. ................. 435/6 |
| 2004/0180357 | A1* | 9/2004 | Reich et al. ............... 514/44 |
| 2005/0233997 | A1* | 10/2005 | Richards et al. ........... 514/44 |

FOREIGN PATENT DOCUMENTS

WO WO 03/049686 * 6/2003
WO WO03073985 A1 * 9/2003

OTHER PUBLICATIONS

Opalinska et al. Nature Reviews Drug Discovery, 2002, vol. 1, p. 503-514.*
Sun et al. Gene Therapy 2001, vol. 8, pp. 638-645.*
Cramer et al. Cell 2003, vol. 112, pp. 645-657.*
Strieter Nature Medicine 2003, vol. 9, pp. 512-513.*
Kalota et al. Handbook of Experimental Pharmacology 2006, vol. 173, pp. 173-196.*
Kojima et al. Current Pharmaceutical Design 2003, vol. 9, pp. 1827-1832.*
Genbank Accession No. NM_001530, Mar. 24, 1999 [retrieved on Oct. 12, 2008]. Retrieved from the internet: <URL:http://www.ncbi.nlm.nih.gov/entrez/viewer.fcgi?db=nuccore&id=194473733>.*
Nguyen et al. Current Opinion in Molecular Therapeutics 2008, vol. 10, pp. 158-167.*
Welsh, S.J., et al., "PX-478, a Potent Inhibitor of Hypoxia-Inducible Factor-1 (HIF-1) and Antitumor Agent," European J. of Cancer, 38(7): S90 (2002).
Tan, Chalet, et al., "Identification of a Novel Small-Molecule Inhibitor of the Hypoxia-Inducible Factor 1 Pathway," Cancer Res., 65(2): 605-612 (2005).
Kong, Dehe, et al., "Echinomycin, a Small-Molecule Inhibitor of Hypoxia-Inducible Dactor-1 DNA-Binding Activity," Cancer Res., 65(19): 9047-9055 (2005).

* cited by examiner

*Primary Examiner*—Tracy Vivlemore
(74) *Attorney, Agent, or Firm*—Elmore Patent Law Group, P.C.; Darlene A. Vanstone; Carolyn S. Elmore

(57) ABSTRACT

Methods for modulating inflammation by administering HIF-1α inhibitors or compounds affecting HIF-1α expression and/or transcriptional activities are disclosed. HIF-1α affecting compounds include compounds that directly inhibit HIF-1α and/or interfere into expression of other proteins and regulation of biochemical pathways that target HIF-1α for degradation in vivo. Also disclosed are methods to enhance the inflammatory response and the destruction of pathogens (e.g., viruses, bacteria) and thereby preventing or minimizing pathogen-induced tissue injury. Also disclosed are methods to enhance the anti-tumor T cell response and the destruction of cancerous tumors and thereby preventing or minimizing metastasis-induced tissue injury. Also provided are methods to accomplish the opposite goal and decrease collateral damage by overactive T cells and thereby protect tissues of vital organs in a novel anti-inflammatory treatment.

8 Claims, 2 Drawing Sheets

MODULATION OF IMMUNE RESPONSE AND INFLAMMATION BY TARGETING HYPOXIA INDUCIBLE FACTORS

RELATED APPLICATION(S)

This application claims the benefit of U.S. Provisional Application No. 60/606,449, filed on Sep. 1, 2004. The entire teaching of the above application is incorporated herein by reference.

GOVERNMENT INTEREST

The present invention was made with the assistance of U.S. Government funding. The U.S. Government has certain rights in this invention.

FIELD OF THE INVENTION

This application relates to the field of immune response, specifically to the use of bioactive agents (compounds) that interfere with HIF-1α expression and/or transcriptional activities and HIF-1α inhibitors and therefore modulate (i.e. decrease or increase) inflammation. These bioactive agents (compounds) include compounds that interfere into expression of other proteins and regulation of biochemical pathways that target HIF-1α for degradation in vivo. The present invention relates to methods to increase inflammation and destruction of pathogens (e.g., viruses, bacteria) and thereby preventing pathogen-induced tissue injury. This application also provides methods to accomplish the opposite goal and decrease collateral damage by overactive immune cells and thereby protect tissues of vital organs in a novel anti-inflammatory treatment.

BACKGROUND OF THE INVENTION

Mammals require molecular oxygen for essential metabolic processes including oxidative phosphorylation in which oxygen serves as electron acceptor during ATP formation. Systemic, local, and intracellular homeostatic responses elicited by hypoxia (the state in which oxygen demand exceeds supply) include erythropoiesis by individuals who are anemic or at high altitude (Jelkmann, Physiol. Rev. 72:449-489, 1992), neovascularization in ischemic myocardium; White et al., Circ. Res. 71:1490-1500, 1992), and glycolysis in cells cultured at reduced oxygen tension (Wolfe et al., Eur. J. Biochem. 135:405-412, 1983). These adaptive responses either increase oxygen delivery or activate alternate metabolic pathways that do not require oxygen. Hypoxia-inducible gene products that participate in these responses include erythropoietin (EPO) (reviewed in Semenza, Hematol. Oncol. Clinics N. Amer. 8:863-884, 1994), vascular endothelial growth factor (VEGF) (Shweiki et al., Nature 359:843-845, 1992; Banai et al., Cardiovasc. Res. 28:1176-1179, 1994; Goldberg & Schneider, J. Biol. Chem. 269:4355-4359, 1994), and glycolytic enzymes (Firth et al., Proc. Natl. Acad. Sci. USA 91:6496-6500, 1994; Semenza et al., J. Biol. Chem. 269:23757-23763, 1994).

The induction of HIF-1α activity by 1% oxygen was detected in many mammalian cell lines (Wang & Semenza, Proc. Natl. Acad. Sci. USA 90:4304-4308, 1993). The EPO enhancer directed hypoxia-inducible transcription of reporter genes transfected into non-EPO-producing cells (Maxwell et al., Proc. Natl. Acad. Sci. USA 90:2423-2427, 1993). RNAs encoding several glycolytic enzymes were induced by 1% oxygen. These experiments support the role of HIF-1α in activating homeostatic responses to hypoxia.

Hypoxia inducible factor-1 (HIF-1) is a mammalian transcription factor expressed uniquely in response to physiologically relevant levels of hypoxia (Wang, G. L., et al., Proc. Natl. Acad. Sci. USA 92:5510-5514, 1995; Wang, G. L., and Semenza, G. L., J. Biol. Chem. 270:1230-1237, 1995; U.S. Pat. No. 5,882,914). HIF-1 is a basic helix loop-helix protein that binds to cis-acting hypoxia-responsive elements of genes induced by hypoxia (Wang, G. L., and Semenza, G. L., Curr. Opin. Hematol. 3:156-162, 1992; Jiang, B. H., et al., J. Biol. Chem. 212:19253-19260, 1997). The genes that are activated by HIF-1 in cells subjected to hypoxia include EPO, vascular endothelial growth hormone (VEGF), heme oxygenase-1, inducible nitric oxide synthase, and glycolytic enzymes aldolase A, enolase 1, lactate dehydrogenase A, phosphofructokinase I, and phosphoglycerate kinase 1 (Semenza, G. L., et al., Kid. Int. 51:553-555, 1997). HIF-1 DNA binding activity and HIF-1 protein concentration increase exponentially as cells are subjected to decreasing oxygen concentrations (Jiang, B. H., et al., Am J. Physiol. 271:C 172-C1180, 1996).

The Hypoxia-Inducible transcription Factor 1α (HIF-1α) has been critically implicated in fundamental and pathophysiological mechanisms of regulation of metabolism and functions of many different types of cells and tissues. The adaptation of mammalian cells to low oxygen conditions is mediated in large part by the transcriptional induction of gene expression. Hypoxia-inducible factor (HIF) is crucial in the transcriptional response of cells to hypoxia. (Semenza G. Nat Rev Cancer 2003, 3, p. 721; Giaccia A, Siim B G, Johnson R S. HIF-1 as a target for drug development. Nat Rev Drug Discov. October 2003; 2(10):803-11).

HIF-1 stability and activity are regulated by post-translational modifications, chaperone function and alternative splicing. Hypoxia-inducible factor (HIF-1) is an oxygen-dependent transcriptional activator, which plays crucial roles in the angiogenesis of tumors and mammalian development. HIF-1 consists of a constitutively expressed HIF-1β subunit and one of three subunits (HIF-1α, HIF-2α or HIF-3α). The stability and activity of HIF-1α are regulated by various post-translational modifications, hydroxylation, acetylation, and phosphorylation. Therefore, HIF-1α interacts with several protein factors including PHD, pVHL, ARD-1, and p300/CBP. Under normoxia, the HIF-1α subunit is rapidly degraded via the von Hippel-Lindau tumor suppressor gene product (pVHL)-mediated ubiquitin-proteasome pathway. The association of pVHL and HIF-1α under normoxic conditions is triggered by the hydroxylation of prolines and the acetylation of lysine within a polypeptide segment known as the oxygen-dependent degradation (ODD) domain. On the contrary, in the hypoxia condition, HIF-1α subunit becomes stable and interacts with coactivators such as p300/CBP to modulate its transcriptional activity. Eventually, HIF-1 acts as a master regulator of numerous hypoxia-inducible genes under hypoxic conditions.

The target genes of HIF-1α are especially related to angiogenesis, cell proliferation/survival, and glucose/iron metabolism. Moreover, it was reported that the activation of HIF-1α is closely associated with a variety of tumors and oncogenic pathways. New evidence suggests that at least two members of the family of hypoxia-inducible factor (HIF) prolyl hydroxylases that regulate HIF stability in response to oxygen availability are themselves also targeted for proteosome-dependent degradation by the E3 ubiquitin ligases Siah1a and Siah2. (Nakayama K, Frew I J, Hagensen M, Skals M, Habelhah H, Bhoumik A, Kadoya T, Erdjument-Bromage H, Tempst P, Frappell P B, Bowtell D D, Ronai Z., Siah2 regulates stability of prolyl-hydroxylases, controls HIF1α abundance, and modulates physiological responses to hypoxia. *Cell.* Jun. 25, 2004; 117(7):851-3.)

HIF-1α activities in myeloid cells are considered to play a pro-inflammatory role since the HIF-1α is required for the inflammatory effects of cells of the innate immune system (Cramer T, Yamanishi Y, Clausen B E, Forster I, Pawlinski R, Mackman N, Haase V H, Jaenisch R, Corr M, Nizet V, Firestein G S, Gerber H P, Ferrara N and Johnson R S. HIF-1alpha is essential for myeloid cell-mediated inflammation. *Cell* 112: 645-657, 2003.).

The inflamed local tissue environments are hypoxic and the tissue damage-associated hypoxia is conducive to accumulation of elevated levels of extracellular adenosine. The recently provided genetic evidence for the critical role of extracellular adenosine and of Gs protein coupled A2A adenosine receptors in down-regulation of activated immune cells in vivo (Ohta A and Sitkovsky M. Role of G-protein-coupled adenosine receptors in downregulation of inflammation and protection from tissue damage. *Nature* 414: 916-920, 2001) suggested that inflammation-induced, local tissue damage-associated hypoxia and oxygen sensors may serve as primary signals of excessive tissue damage in order to de-activate immune cells.

SUMMARY

The invention is a method for treating a subject in need thereof to increase one or more indicia of either cell mediated immunity, humoral immunity, or innate resistance to infection, comprising the step of administering an effective amount of at least one HIF-1α-affecting compound to the subject under conditions suitable for inducing said increase in said indicia, wherein said HIF-1α-affecting compound is selected from the group consisting of a compound capable of inhibiting expression and functions of HIF-1α, a compound which inhibits HIF-1α, a compound which interferes with HIF-1α gene expression, and a compound which inhibits the PHD1,2,3 gene expression. In addition, compounds are selected among compounds that interfere with the activities of other proteins that regulate activities of PHD1,2,3 by activating or stabilizing the E3 ubiquitin ligases Siah1 and Siah2.

In the practice of the method, it may further comprise administering the at least one HIF-1α-affecting compound to the subject under conditions effective to increase a number, a percentage, a ratio of percentages or an activity of blood cells in a sample of a biological fluid or a tissue from a pre-treatment value to a higher post-treatment value or effective to increase a concentration of a blood protein in a sample of biological fluid from a pre-treatment value to a higher post-treatment value. The blood cells can be selected from among leukocytes, lymphocytes, monocytes, T-lymphocytes, B-lymphocytes, stem cells, $CD2^+$-lymphocytes, $CD4^+$-lymphorytes, $CD8^+$-lymphocytes, $CD19^+$-lymphocytes, plasma cells, neutrophils, stab neutrophils, segmented neutrophils, basophils, eosinophils, platelets, and erythrocytes.

Where the blood protein level is being compared, the blood protein is selected from among an immunoglobulin, a lysozyme, a cytokine, an interferon, a complement protein, a coagulation protein, a fibrinolytic system protein, an enzyme inhibitor, a bradykinin system protein, a hormone, a cytokine, and a receptor protein. Immunoglobulins may be selected from among an IgG, IgA, IgM, IgD, and an immunoglobulin capable of binding an antigen.

In one embodiment, the method further comprises administering the at least one HIF-1α-affecting compound to the subject under conditions effective to increase a number or a percentage of blood cells in a sample of biological fluid from a pre-treatment value to a higher, post treatment value. The subject includes but is not limited to an immunocompromised subject from selected from the group consisting of: a patient having an infectious disease selected from the group consisting of: a bacterial infection, a viral infection, a mycoplasma infection, a parasitic infection, an opportunistic infection, an pneumocystis infection, a cytomegalovirus infection, a herpes virus infection, a mycobacterium infection, or a human immunodeficiency virus infection; a patient exposed to radiation or one or more chemotherapeutic antiproliferative drugs; a patient having a transplant, cancer, cancerous tissues, tumor metastases, debulked cancerous tissues, remaining undetected tumor metastasis, autoimmune disease, systemic lupus erythematosus, rheumatoid arthritis, Sjogren's syndrome, multiple sclerosis, Crohn's disease, ulcerative colitis, inflammatory bowel disease, osteoporosis, type I diabetes mellitus including the destruction of pancreatic islets leading to diabetes and the inflammatory consequences of diabetes, including leg ulcers, or at an increased relative risk of developing type 1 insulin-dependent diabetes mellitus; a patient having a primary or a secondary immune deficiency disease; a patient having a staphylococcal infection, pyoderma, furunculitis, cellulitis, eczema, acne vulgaris, psoriasis, contact dermatitis, or infection skin ulcers; a patient having gingivitis, dental caries, or periapical granulomas; a patient having a gynecological infection, pelvic inflammatory disease, endometriosis, infertility caused by endometriosis, cervicitis, vaginitis, tubular or ovarian abscess or an adnexal abscess; a patient having lymphangitis or an infralymphatic infection; a patient having an acute or chronic respiratory disease, upper airways disease, sinusistis or parasinusitis, or rhinovirus or influenza infection; a patient having an allergic disease selected from the group consisting of: asthma, hay fever, rhinitis, vernal conjunctivitis and other eosinophil-mediated conditions; a patient having otitis media, conjunctivitis, uveitis or keratitis; a patient having an organ, tissue or cell transplantation, a transplant rejection, or graft versus host disease; a patient having adverse effects from drug therapy, including adverse effects from amphotericin B treatment, adverse effects from immunosuppressive therapy, stomatitis and mucositis due to immunosuppression; a patient having cardiovascular conditions including circulatory diseases induced or exasperated by an inflammatory response, such as ischemia, atherosclerosis, peripheral vascular disease, inflammatory aortic aneurysm, vasculiti; stroke; spinal cord injury; congestive heart failure; hemorrhagic shock, ischemia/reperfusion injury, vasospasm following subarachnoid hemorrhage, vasospasm following cerebrovascular accident, pleuritis, pericarditis, cardiovascular complications of diabetes and restenosis following angioplasty stent placement, shunt placement or grafting; a patient having dialysis, including pericarditis, due to peritoneal dialysis; a patient having gout; a patient having chemical or thermal trauma; and an immunocompromised patient at an increased relative risk of developing an infection.

In accordance with the invention, the increase in the number of the blood cells in the sample of peripheral blood is selected from among: an increase in leukocytes of by about 1.1-fold to about 1.6-fold; an increase in lymphocytes of by about 1.1-fold to about 2.4-fold; an increase in $CD2^+$-lymphocytes by about 1.1-fold to about 2.6-fold; an increase in $CD4^+$-lymphocytes by about 1.1-fold to about 6.4-fold; an increase in $CD8^+$-lymphocytes by about 1.1-fold to about 2.5-fold; an increase in $CD19^+$-lymphocytes by about 1.1-fold to about 2.3-fold; an increase in surface immunoglobulin positive B-lymphocytes by about 1.1-fold to about 1.6-fold; an increase in E-rosette forming T-lymphocytes by about 1.1-fold to about 1.8-fold; an increase in neutrophils by about 1.1-fold to about 1.4-fold; an increase in a CD4+/CD8+ ratio by about 1.1-fold to about 1.8-fold; and, an increase in monocytes by about 1.1-fold to about 1.4-fold.

In another embodiment, the invention is a method to protection from the pathogen-induced tissue by administering an HIF-1α inhibitor, a bioactive agent which stabilizes expression of HIF-1α and/or a bioactive agent which increases activities of HIF-1α-degrading proteins and, in particular, wherein the HIF-1α inhibitor is a small interfering RNA (siRNA) or a ribozyme.

In another embodiment, the invention is a method for treating tumors comprising the step of administering an effective amount of at least one targeted HIF-1α inhibitor. In one such embodiment, the at least one targeted HIF-1α inhibitor is synthetic or natural compounds that activate or stabilize E3 ubiquitin ligases Siah1 and Siah2.

In yet another embodiment, the invention provides a method where the targeted inhibition of HIF-1α in activated T cells, in order to enhance their effector functions and pathogen- or cancerous tumor-destroying activities, can be combined with the inhibition of indoleamine 2,3-dioxygenase (IDO) activity to further prevent negative regulation of T cells and even more enhance their effector functions and pathogen- or cancerous tumor-destroying activities.

IDO was shown to affect T cells activation most likely due to depletion of the essential amino acid tryptophan (*The Journal of Immunology*, 2002, 168: 3771-3776. *Cells Expressing Indoleamine 2,3-Dioxygenase Inhibit T Cell Responses* Andrew L. Mellor, Derin B. Keskin, Theodore Johnson, Phillip Chandler and David H. Munn) Accordingly, pharmacological inhibitors of HIF-1α and IDO or genetic manipulation of HIF-1α and IDO (e.g. RNA interference, ribozymes and the like) may be used in combination in the therapies of viral or bacterial infections and in immunotherapies of tumors when there is a need to "de-inhibit" T cells by preventing negative regulation by natural physiological mechanisms and achieve the maximal possible activity of T cells.

DETAILED DESCRIPTION OF THE INVENTION

Figure 1:
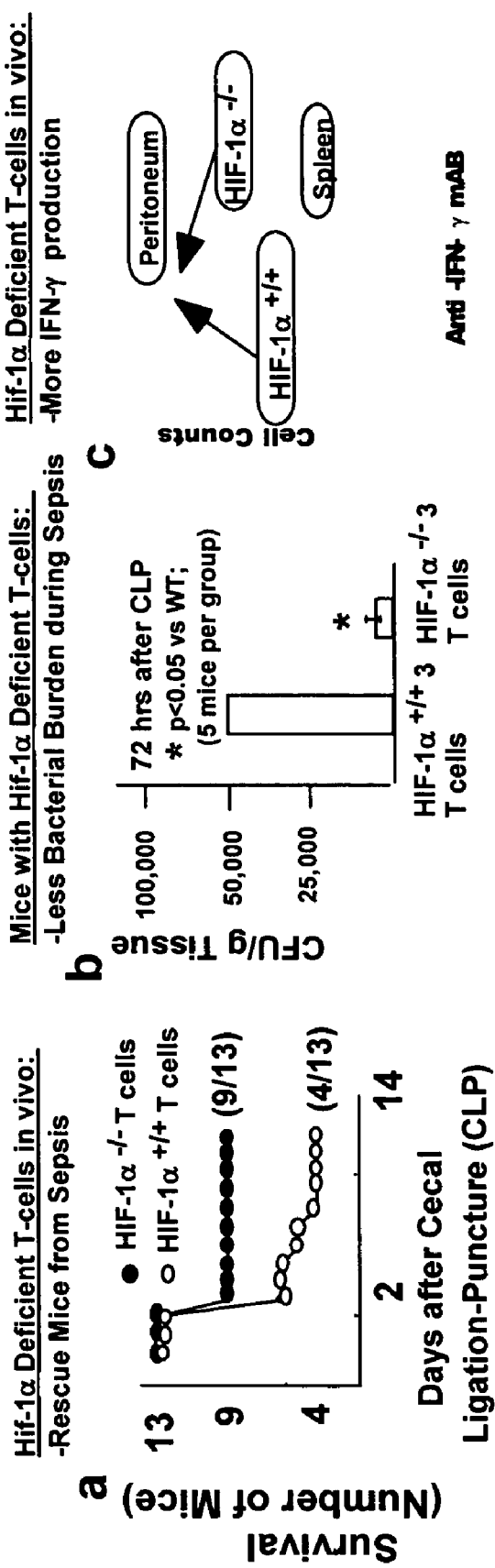
FIG. 1A depicts the increased survival of septic mice due to targeted deletion of HIF-1α gene in T cells.
FIG. 1B depicts strong clearing of bacterial infections in mice with deletion of HIF-1α gene in T cells.
FIG. 1C depicts increased production of anti-bacterial cytokine IFN-γ in vivo in mice with T cell selective deletion of HIF-1α.
Figure 2:
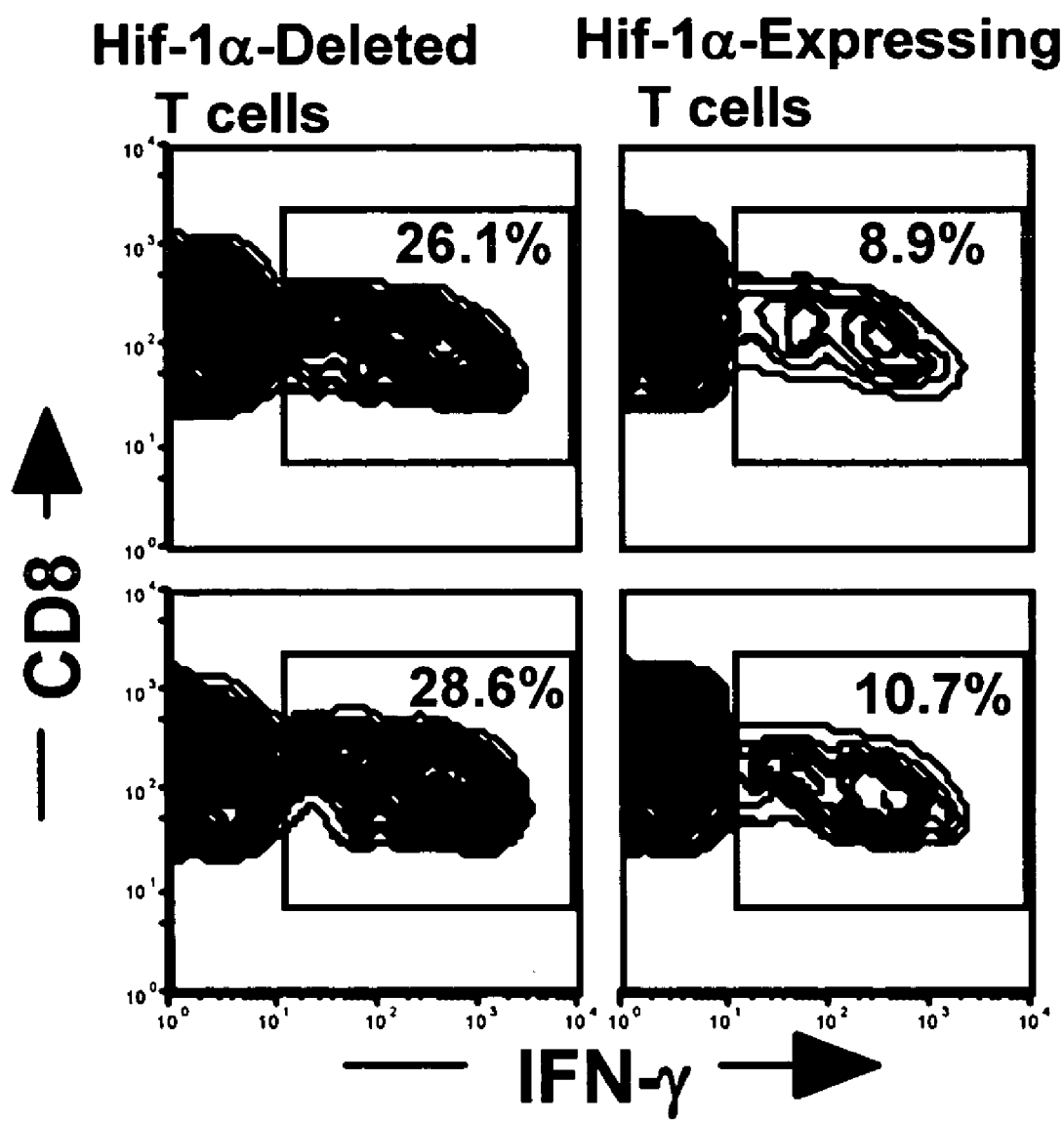
FIG. 2 depicts another experiment with strong increase in TCR-triggered IFN-γ secretion in mice with T cell selective deletion of HIF-1α.

The applicant has surprisingly discovered the opposite effects, that is, an anti-inflammatory effect of HIF-1α expression in T cells. Circulating peripheral T cells are strategically pre-positioned to mount immediate pro-inflammatory response after activation with bacterial superantigens. T cells and other immune cells could be influenced by the complex milieu of signaling molecules in different tissues. This invention exploits this surprising discovery of anti-inflammatory properties of HIF-1α in T cells, which are different from described for its role in cells of innate immune system, where HIF-1α is considered pro-inflammatory. Using a new methodology, the applicant has accomplished the targeted deletion of HIF-α gene in T-cells in mice. The invention relates to novel methods of treatment, prevention or diagnosis of conditions due to the immune response, inflammation and tissue damage by administering a compound to treat, prevent and diagnose diseases such as those due to inappropriate, excessive or not-terminated activities of immune cells. The invention also relates to the treatment, prevention and diagnosing diseases arising from the survival of a pathogen (for example, bacteria and viruses) because of insufficient, short-lived and/or prematurely terminated activities of immune cells.

Diseases treatable in accordance with this aspect of the of the invention include but are not limited to: sepsis, septic shock, encephalitis, infectious arthritis, endotoxic shock, gram negative shock, Jarisch-Herxheimer reaction, shingles, chicken pox, small pox, toxic shock, cerebral malaria, bacterial meningitis, acute respiratory distress syndrome (ARDS), severe acute respiratory syndrome (SARS), tuberulosis (TB), lyme disease, HIV infection, (TNFα. -enhanced HIV replication, and TNF-α inhibition of reverse transcriptase inhibitor activity.

The invention is based on the unexpected discovery that mice with selective genetic deletion of Hypoxia-Inducible Factor-1α (HIF-1α) gene in T cells are rescued from bacterial sepsis. The elimination of HIF-1α in T cells resulted in increased levels of anti-bacterial IFN-γ, in a decreased bacterial burden and decreased bacteria-induced tissue damage. These effects of targeted HIF-1α inactivation have established HIF-1α as critical in physiological down-regulation of T cells in inflamed hypoxic tissues. This, in turn, suggests that the targeted inhibition of HIF-1α can be used to enhance T cell responses, while the stabilization and/or enhancement of HIF-1α activities can be used to inhibit T cell response. These observations are completely different from the state-of the art views, where HIF-1α is believed to be required for the pro-inflammatory response. These data provided in vivo proof of the principle that the targeted inactivation of HIF-1α and/or other hypoxia inducible factors (e.g. HIF-2 and HIF-3, notably HIF-2α and HIF-3α) in T cells represents a novel method to "de-inhibit" immune cells in vivo and thereby strongly improve their effector anti-pathogen functions. These data also provided a proof of principle that similar approach can be used to modulate functions of myeloid cells.

The present invention provides methods to increase inflammation and anti-pathogen (e.g. anti-viral and anti-bacterial) activity of T cells and thereby accomplish the prevention of the pathogen-induced tissue injury and thereby treat infectious diseases.

In an opposite application, the use of bioactive agents, compounds or treatments that stabilize HIF-1α provides methods to decrease activity of T cells and thereby protect tissues of vital organs from excessive collateral damage by activated T cells. These methods to manipulate activity of T cells are based on the use of bioactive agents that interfere with HIF-1α expression and/or HIF-1α transcriptional activities as well as using HIF-1α inhibitors. These bioactive agents include not only compounds that interfere into expression and activity of HIF-1α, but also in the expression and activities of other proteins that are involved in HIF-1α degradation in vivo. These proteins include, but not limited to e.g. prolyl hydroxylases (PHD) enzymes that degrade HIF-1 and Siah proteins that function as regulators of PHD expression. Together, molecules of HIF-1, HIF-2, HIF-3, PHD and Siah proteins represent important targets to modulate inflammation and accomplish treatments of inflammatory diseases and infectious diseases.

The method of the invention involves administering compounds capable of inhibiting expression and functions of HIF-1α, interfering with HIF-1α, gene expression or facilitating HIF-1α degradation in order to improve anti-bacterial and anti-viral activity of T cells and of other immune cells thereby useful as anti-bacterial or anti-viral bioactive agents.

In one embodiment, the method of the invention involves the administration of synthetic or natural compounds that have properties of competitive and/or non-competitive inhibitors of (a) HIF-1α binding to DNA and preventing heterodimerization and/or interactions of HIF-1α with other important proteins and/or (b) E3 ubiquitin ligases Siah1 and Siah2 to prevent Siah1 and Siah2-mediated degradation of PHD and therefore these compounds prolong and enhance the PHD-mediated degradation of HIF-1α and lead to inhibition of HIF-1α activities. In other embodiments, the method of the invention involves synthetic or natural compounds that have properties of activators or stabilizers of prolylhydroxylases PHD 1,2,3 (which function to target HIF for degradation). In the case, without being bound to a single theory, applicant believes that such compounds achieve their efficacy by prolonging and enhancing the PHD-mediated degradation of HIF-1α thereby leading to inhibition of undesirable HIF-1α activities.

In certain aspects, the methods of the invention increase an immune response, inflammation and thereby accomplish protection from the pathogen-induced tissue damage by administering either an HIF-1α inhibitor or bioactive agent (e.g. small interfering RNA (siRNA) or ribozyme) that destroys HIF-1α expression or bioactive agents that stabilize expression of HIF-1α and/or increase activities of HIF-1α-degrading proteins (e.g. PHD1,2,3) and thereby facilitate degradation of HIF-1α. Suitable compounds for use in the invention include but are not limited to i) inhibitors of Siah1a/2 proteins can be used to prevent degradation of PHD and thereby increase degradation of HIF-1 and accomplish an increase of T cell response; ii) activators of PHD enzymes can be used to increase degradation of HIF-1α; and iii) inhibitors of HIF-1α can be used to increase T cell functions. Applicant has realized that the blocking of HIF-1α itself or HIF-1α interacting proteins inhibit tumor growth. Based on these findings, HIF-1α can be a prime target for anticancer therapies. In contrast to prevailing view that HIF-1 should be targeted inside of tumor cells to promote their death due to apoptosis or necrosis, Applicant realized that HIF-1 should be also destroyed inside of anti-tumor T cells, so that these anti-tumor T cells will not be prevented from killing tumor cells in hypoxia microenvironment of solid tumors. Thus, the method is suggested where compounds that prevent HIF-1α expression and activities should be used at the time of anti-tumor immune attack by anti-tumor T cells to synergize in destruction of tumors.

In yet another aspect of the invention, the methods to decrease an immune response, inflammation and thereby accomplish protection of vital organs from the immune cell-induced collateral tissue damage by administering either an HIF-1α stabilizer or bioactive agents that inhibit the expression of HIF-1α-degrading molecules (e.g. but not limited to prolyl hydroxylases, PHD). Suitable compounds include but are not limited to i) activators of Siah1a/2 proteins can be used to enhance degradation of PHD and thereby decrease degradation of HIF-1α and lead to an inhibition of T cell response; ii) inhibitors of PHD enzymes can be used to decrease degradation of HIF-1α and lead to an inhibition of T cell response; and iii) activators of HIF-1α can be used to decrease T cell functions.

In yet another aspect the invention includes a method for treating a disease which could be alleviated by the decrease in an HIF-1α activity in a subject in need of such treatment, comprising administering to the subject a therapeutically effective amount of an HIF-1α inhibitor or bioactive agent, for example, small interfering RNA (siRNA) that destroys HIF-1α expression or bioactive agent that accelerates and facilitates degradation of HIF-1α.

In still another aspect, the invention includes a method for treating a disease, which could be alleviated by the increase in HIF-1α activity in a subject in need of such treatment, comprising administering to the subject a therapeutically effective amount of an HIF-1α activator or stabilizer or bioactive agent, for example, small interfering RNA (siRNA) that stabilizes HIF-1α expression or bioactive agents that prevent degradation of HIF-1α by interfering with expression and/or activities of Siah1a/2 proteins or PHD.

The invention includes methods wherein the targeted HIF-1α inhibition employs synthetic or natural compounds that have properties of activators or stabilizers of E3 ubiquitin ligases Siah1 and Siah2 to facilitate Siah1 and Siah2-mediated degradation of prolylhydroxylases PHD 1,2,3 (which function to target HIF for degradation). Without being bound to a single theory, applicant believes that such compounds achieve their efficacy by preventing the PHD-mediated degradation of HIF-1α thereby leading to stabilization of HIF-1α and prolongation of HIF-1α activities in order to modulate immune response.

Disclosed are methods for treating a disease associated with an HIF-1α in a subject in need of such treatment, comprising administering to the subject a therapeutically effective amount of an HIF-1α affecting compound.

In still another aspect, a method for treating a disease associated with an HIF-1α in a subject in need of such treatment is disclosed wherein disease is associated with interruption of the local blood supply and/or decrease of local oxygen tension and/or disregulation of cell metabolism.

Of particular interest and efficacy is the use of these methods to treat inflammatory responses due to organ, tissue or cell transplantation, i.e., the transplantation of allogenic or xenogenic tissue into a mammalian recipient, autoimmune diseases and inflammatory conditions due to circulatory pathologies and the treatment thereof, including angioplasty, stent placement, shunt placement or grafting with the pathology or trauma that initiates the inflammatory response. Also, the invention relates to methods to adoptively transferred anti-tumor T cells capable of increasing production by T cells of cytokine IFN-γ with anti-tumor activities. Further, this can be accomplished by the administration of bioactive agents that inhibit or destroy HIF-1α expression.

In one application, a patient with immunogenic tumors will be given injections (i.e., adoptive transfer) of his own anti-tumor T cells which were expanded in vitro. The injected T-cells are capable of recognizing and be activated by his tumor. The tumors will be then destroyed because (1) of direct killing by these T cells and/or (2) they are "starved" due to a decreased blood supply. The decreased blood supply to tumors is because T cells can produce IFN-γ, which, in turn, prevents pro-tumor neovascularization. In accordance with the discovery that HIF-1α inhibits IFN-γ production by T cells, the inhibition of HIF-1α in adoptively transferred anti-tumor T cells will release T cells from HIF-1-mediated suppression and will lead to much higher levels of IFN-γ and tumor rejection. In the practice of the invention, combinations of compounds and the methods of the invention are also employed.

Unless explained otherwise, all technical and scientific terms used herein have the same meaning as commonly understood to one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Methods and materials similar or equivalent to those described herein can be used in the practice or testing of the present disclosure. The materials, methods, and examples are illustrative only and not intended to be limiting.

As used herein, relevant terms include:

Hypoxia is the state in which oxygen demand exceeds supply.

HIF-1α, is Hypoxia Inducible factor 1α.

PHD are members of the family of hypoxia-inducible factor (HIF) prolyl hydroxylases that regulate HIF stability in response to oxygen availability.

Siah1a and Siah2 are E3 ubiquitin ligases that target molecules of PHD for proteosome-dependent degradation.

pVHL, is von Hippel-Lindau tumor suppressor gene product, which is involved in pVHL-mediated ubiquitin-proteasome pathway of degradation of HIF-1α.

p300/CBP is a coactivator that interacts with HIF-1α in the hypoxia condition to modulate its transcriptional activity.

IFN-γ is a cytokine with many different effects on different cells.

CLP, is cecal ligation and puncture (CLP) procedure to induce bacterial sepsis.

Adjuvant: Any agent that enhances or increases one or more immune-stimulating properties of another agent (such as a chemical compound or antigenic epitope). An adjuvant augments, stimulates, activates, potentiates, or modulates the immune response at the cellular or humoral level.

For example, addition of an adjuvant to a vaccine improves the immune response of a cell, such as a cell in a subject. An adjuvant can be used so that less vaccine is needed to produce the immune response. One specific, non-limiting example of an adjuvant is Freund's adjuvant, which is a water-in-oil emulsion that contains an immunogen, an emulsifying agent and mycobacteria. The classical agents (Freund's adjuvant, BCG, *Corynebacterium parvum*) contain bacterial antigens. Some adjuvants are endogenous (e.g. histamine, interferon, transfer factor, tuftsin, interleukin-1 and interleukin-12). The mode of action of an adjuvant can be non-specific, resulting in increased immune responsiveness to a wide variety of antigens, or antigen-specific, i.e. affecting a restricted type of immune response to a narrow group of antigens. The therapeutic efficacy of many biological response modifiers is related to their antigen-specific immunoadjuvanticity.

Agent: Any polypeptide, compound, small molecule, organic compound, salt, polynucleotide, peptidomimetic, or other molecule of interest.

Animal: Living multi-cellular vertebrate organisms, a category that includes, for example, mammals and birds. The term mammal includes both human and non-human mammals. Similarly, the term "subject" includes both human and veterinary subjects.

Antisense, Sense, and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T). Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Antisense oligonucleotide: A sequence of at least about 8 nucleotides, such as about at least 10, 12, 15, 20, 30 or 50 nucleotides, wherein the sequence is from a gene sequence (such as all or a portion of a cDNA or gene sequence, or the reverse complement thereof), arranged in reverse orientation relative to the promoter sequence in a transformation vector.

Autoimmune disorder: A disorder in which the immune system produces an immune response (e.g. a B cell or a T cell response) against an endogenous antigen, with consequent injury to tissues.

Biological samples: Suitable biological samples include samples containing genomic DNA, RNA (including mRNA), and/or protein, obtained from cells of a subject. Examples include, but are not limited to, peripheral blood, urine, semen, saliva, tissue biopsy, surgical specimen, amniocentesis samples, derivatives and fractions of blood such as serum, and biopsy material.

Cancer: Malignant neoplasm that has undergone characteristic anaplasia with loss of differentiation, increase rate of growth, invasion of surrounding tissue, and is capable of metastasis.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Comprises: A term that means "including." For example, "comprising A or B" means including A or B, or both A and B, unless clearly indicated otherwise.

Cytokine: Proteins made by cells that affect the behavior of other cells, such as lymphocytes. In one embodiment, a cytokine is a chemokine, a molecule that affects cellular trafficking.

DNA: Deoxyribonucleic acid. DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Deletion: The removal of a sequence of DNA, the regions on either side being joined together.

Differentiation: The process by which cells become more specialized to perform biological functions. Differentiation is a property that is totally or partially lost by cells that have undergone malignant transformation.

Epitope: An antigenic determinant. These are particular chemical groups or peptide sequences on a molecule that are antigenic, i.e. that elicit a specific immune response. An antibody binds a particular antigenic epitope.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Hypersensitivity: Immune responses to innocuous antigens that lead to symptomatic reactions upon re-exposure are called hypersensitivity reactions. These can cause hypersensitivity diseases if they occur repetitively. This state of heightened reactivity to an antigen is called hypersensitivity. Hypersensitivity reactions are classified by mechanism: type I hypersensitivity reactions involve IgE antibody triggering of mast cells; type II hypersensitivity reactions involve IgG antibodies against cell-surface or matrix antigens; type III hypersensitivity reactions involve antigen:antibody complexes; and type iV hypersensitivity reactions are T cell-mediated.

Immune cell: Any cell involved in a host defense mechanism, such as cells that produces pro-inflammatory cytokines, and such as cells that participate in tissue damage and/or disease pathogenesis. Examples include, but are not limited to: T cells, B cells, natural killer cells, neutrophils, mast cells, macrophages, antigen-presenting cells, basophils, and eosinophils.

Immune response: A response of a cell of the immune system, such as a B cell or T cell, to a stimulus. In one embodiment, the response is specific for a particular antigen (an "antigen-specific response"). In one embodiment, an immune response is a T cell response, such as a Th1, Th2, or Th3 response.

Inflammation: When damage to tissue occurs, the body's response to the damage is usually inflammation. The damage can be due to trauma, lack of blood supply, hemorrhage, autoimmune attack, transplanted exogenous tissue or infection. This generalized response by the body includes the release of many components of the immune system (e.g. IL-1 and TNF), attraction of cells to the site of the damage, swelling of tissue due to the release of fluid and other processes.

Inflammation, the response of tissue to injury, is divided into two phases, termed acute and chronic. In the acute phase, inflammation is characterized by increased blood flow and vascular permeability, accumulation of fluid, and accumulation of leukocytes and inflammatory mediators (e.g. cytokines). In the subacute/chronic phase, inflammation is characterized by the development of specific humoral and cellular immune responses to the pathogen(s) present at the site of tissue injury. During both the acute and chronic inflammatory processes, a variety of soluble factors are involved in leukocyte recruitment through increased expression of cellular adhesion molecules and chemoattraction. Many of these soluble mediators regulate the activation of both the resident cells (such as fibroblasts, endothelial cells, tissue macrophages, and mast cells) and newly recruited inflammatory cells (such as monocytes, lymphocytes, neutrophils, and eosinophils).

Leukocyte: Cells in the blood, also termed "white cells," that are involved in defending the body against infective organisms and foreign substances. Leukocytes are produced in the bone marrow. There are 5 main types of white blood cells, subdivided between 2 main groups: polymorphonuclear leukocytes (neutrophils, eosinophils, basophils) and mononuclear leukocytes (monocytes and lymphocytes). When an infection is present, the production of leukocytes increases.

Lymphocytes: A type of white blood cell that is involved in the immune defenses of the body. There are two main types of lymphocytes: B-cells and T-cells.

Mammal: This term includes both human and non-human mammals. Similarly, the term "subject" includes both human and veterinary subjects.

Monoclonal antibody: An antibody produced by a single clone of B-lymphocytes. Monoclonal antibodies are produced by methods known to those of skill in the art, for instance by making hybrid antibody-forming cells from a fusion of myeloma cells with immune spleen cells.

Natural killer (NK) cell: These are large, usually granular, non-T, non-B lymphocytes, which kill certain tumor cells. NK cells are important in innate immunity to viruses and other intracellular pathogens, as well as in antibody-dependent cell-mediated cytotoxicity (ADCC).

Neoplasm: An abnormal mass of tissue that results from excessive cell division hat is uncontrolled and progressive, also called a tumor. Neoplasms can be begin (neither infiltrative nor cancerous) or malignant (invasive).

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide: A linear polynucleotide sequence of up to about 200 nucleotide bases in length, for example a polynucleotide (such as DNA or RNA) which is at least 6 nucleotides, for example at least 15, 25, 50, 75, 100 or even 200 nucleotides long.

Pharmaceutical agent: A chemical compound or composition capable of inducing a desired therapeutic or prophylactic effect when properly administered to a subject or a cell. "Incubating" includes a sufficient amount of time for an agent to interact with a cell. "Contacting" includes incubating an agent in solid or in liquid form with a cell.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of adenosine receptor modulators.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: Any chain of amino acids, regardless of length or post-translational modification (e.g. glycosylation or phosphorylation).

Preventing or treating a disease: "Preventing" a disease refers to inhibiting or decreasing the full development of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. "Treatment" refers to a therapeutic intervention that ameliorates a sign or symptom of a disease or pathological condition after it has begun to develop.

Purified: The term purified does not require absolute purity; rather, it is intended as a relative term. Thus, for example, a purified peptide or nucleic acid preparation is one in which the peptide or nucleic acid is more enriched than the peptide or nucleic acid is in its natural environment within a cell. Preferably, a preparation is purified such that the protein or nucleic acid represents at least 50% of the total peptide or nucleic acid content of the preparation.

Receptor: A molecular structure within a cell or on the surface of a cell, characterized by selective binding of a specific substance and a specific physiological effect that accompanies the binding, for example, cell surface receptors for peptide hormones, neurotransmitters, immunoglobulins, small molecules, and cytoplasmic receptors for steroid hormones. An adenosine receptor is a cell surface receptor for adenosine, and includes, but is not limited to, the A2 or A3 receptors.

Ribozyme: Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs can be used to confer RNA cleaving activity on the antisense RNA, such that endogenous mRNA molecules that bind to the antisense RNA are cleaved, which in turn leads to an enhanced antisense inhibition of endogenous gene expression.

Specific binding agent: An agent that binds substantially only to a defined target. Thus an antibody or antibody fragment-specific binding agent binds substantially only the defined antibody or antibody fragment, or an antibody region within a protein, such as a fusion protein. As used herein, the term "adenosine receptor specific binding agent," includes anti-adenosine receptor antibodies (and functional antibody fragments thereof) and other agents (such as potential therapeutic agents) that bind substantially only to adenosine receptors.

Antibodies can be produced using standard molecular procedures described in a number of texts, including Harlow and Lane (*Antibodies, A Laboratory Manual*, CSHL, New York, 1988). The determination that a particular agent binds substantially only to the target protein or peptide can readily be made by using or adapting routine procedures. One suitable in vitro assay makes use of the Western blotting procedure (Harlow and Lane, *Antibodies, A Laboratory Manual*, CSHL, New York, 1988).

Shorter fragments of antibodies can also serve as specific binding agents. For instance, FAbs, Fvs, and single-chain Fvs (SCFvs) that bind to adenosine receptor would be adenosine receptor-specific binding agents.

Subject: Living multi-cellular vertebrate organisms, a category that includes both human and non-human mammals.

T Cell: A white blood cell involved in the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

Target sequence: A portion of ssDNA, dsDNA or RNA that, upon hybridization to a therapeutically effective oligonucleotide or oligonucleotide analog, results in the inhibition of gene expression, such as adenosine receptor gene expression. An antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Therapeutically effective amount: A quantity of an agent or composition sufficient to achieve a desired effect in a subject being treated. For instance, this can be the amount necessary to increase activity of an immune cell and/or enhance an immune response in a subject. In one example, it is an amount that will inhibit viral, fungal, or bacterial replication or to measurably alter outward symptoms of the viral, fungal, or bacterial infection. In another example, it is an amount that will decrease or prevent further tumor growth. When administered to a subject, a dosage will generally be used that will achieve target tissue concentrations (for example, in lymphocytes) that has been shown to achieve in vitro inhibition of viral replication or reduction of tumor cells.

Therapeutically effective dose: A dose sufficient to prevent advancement, or to cause regression of the disease, for example a dose sufficient to reduce the volume or size of a tumor. In another example, it is an amount which is capable of relieving symptoms caused by a disease, such as pain or swelling.

Therapeutically effective adenosine receptor oligonucleotides and oligonucleotide analogs: Characterized by their ability to inhibit or decrease expression of adenosine receptors. As described below, complete inhibition is not necessary for therapeutic effectiveness. Therapeutically effective oligonucleotides are characterized by their ability to inhibit or decrease the expression of adenosine receptors. Inhibition is a reduction in adenosine receptor expression observed when compared to adenosine receptor production in the absence of the oligonucleotide or oligonucleotide analog. For example, an oligonucleotides may be capable of inhibiting the expression of adenosine receptors by at least 15%, 30%, 40%, 50%, 60%, or 70%, or more, and still be considered to be therapeutically effective.

Therapeutically effective oligonucleotides and oligonucleotide analogs are additionally characterized by being sufficiently complementary to adenosine receptor-encoding nucleic acid sequences. As described herein, sufficient complementary means that the therapeutically effective oligonucleotide or oligonucleotide analog can specifically disrupt the expression of adenosine receptors, and not significantly alter the expression of genes other than adenosine receptors.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Treatment: Refers to both prophylactic inhibition of initial infection, and therapeutic interventions to alter the natural course of an untreated disease process, such as infection with a virus.

Tumor: An abnormal mass of tissue that results from excessive cell division that is uncontrolled and progressive, also called a neoplasm. Tumors can be benign (neither infiltrative nor cancerous) or malignant (invasive).

Vaccine: A dead or attenuated (non-pathogenic) form of a pathogen, or an antigen isolated from a pathogen, administered to a subject to induce adaptive immunity to the pathogen.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art. The term "vector" includes viral vectors, such as adenoviruses, adeno-associated viruses, vaccinia, and retroviruses vectors.

It will be appreciated by those skilled in the art that the conclusions reached in studies of cecal ligation sepsis model reach beyond this particular model to include the pathogenesis of other major diseases with an inflammatory compound. It will be understood that the particular embodiments of the invention are shown by way of illustration and not as limitations of the invention. The principle features of this invention can be employed in various embodiments without departing from the scope of the invention.

The present invention pertains to methods for treating inflammatory diseases in a mammal. The methods include administration of a therapeutically effective amount of bioactive agent that prevents HIF-1α action or facilitates HIF-1α action.

The invention provides methods of treatment of adverse effects of pathogen infection by enhancing anti-pathogen activities of T cells. The emphasis on T cells in development of anti-bacterial treatments is an unusual and novel approach since the majority of studies of the immune response to bacterial infections and sepsis have been focused on cells of the innate immune system.

Inflamed local tissue environments are hypoxic and the tissue damage-associated hypoxia is conducive to accumulation of elevated levels of extracellular adenosine. The recently provided genetic evidence for the critical role of extracellular adenosine and of Gs protein coupled A2A adenosine receptors in down-regulation of activated immune cells in vivo (Ohta A and Sitkovsky M. Role of G-protein-coupled adenosine receptors in downregulation of inflammation and protection from tissue damage. *Nature* 414: 916-920, 2001) suggested that inflammation-induced local tissue damage-associated hypoxia and oxygen sensors may serve as primary signals of excessive tissue damage in order to de-activate immune cells.

In this study the question was asked whether selective inactivation of HIF-1α in T cells in vivo will affect the course of disease in a clinically relevant model of bacterial infection and sepsis after cecal ligation and puncture (CLP) (Ebong S, Call D, Nemzek J, Bolgos G, Newcomb D and Remick D. Immunopathologic alterations in murine models of sepsis of increasing severity. *Infect Immun* 67: 6603-6610, 1999.). To enable the investigation of the possible role of T cells in clearing septic bacterial infections, we have adapted a murine model of sepsis, which results in 50% mortality after 72 hours of cecal ligation and puncture (CLP). By avoiding the early (<24 hour) lethal events of sepsis enabled us to study the behavior of T cells, which may have required longer than 24 hrs to be recruited and activated in inflamed environments. The results revealed a previously unappreciated anti-bacterial capacities of T cells in hypoxic inflamed tissue microenvironments during intra-abdominal sepsis and the critical role of HIF-1α in regulating anti-bacterial activities of T cells.

EXAMPLES

Introduction

The use of the hypoxic marker EF5 allowed to demonstrate (data not shown) that both CD4+ and CD8+ T cells were indeed exposed to hypoxic (<1% oxygen tension) inflamed areas of peritoneum. Both splenic and peritoneal granulocytes were also exposed to very low oxygen tension, suggesting their compartmentalization in hypoxic regions of the peritoneum and the spleen. It was important to determine whether location of T cells in hypoxic areas of inflamed tissues and organs may affect their functions since no data have been provided so far to suggest the relevance of T cells functions in hypoxic inflamed areas during sepsis as it is related to the final outcome of attempts of the immune system to destroy bacterial pathogens. Since we have shown that T cells are recruited and are present in hypoxic areas of inflamed tissues, we hypothesized that these T cells were activated e.g. by bacterial products, but were inhibited in local inflamed and hypoxic environment and therefore prevented from contribution to pathogen destruction due to the negative regulation by hypoxia-stabilized and TCR-activation induced HIF-1α.

To test this hypothesis we created mice with T-cell specific deletion of HIF-1α. This was facilitated by the availability of genetically altered mice where HIF-1α gene was modified with 5' and 3' loxP restriction sites (Cramer T, Yamanishi Y, Clausen B E, Forster I, Pawlinski R, Mackman N, Haase V H, Jaenisch R, Corr M, Nizet V, Firestein G S, Gerber H P, Ferrara N and Johnson R S. HIF-1alpha is essential for myeloid cell-mediated inflammation. *Cell* 112: 645-657, 2003). The absence or deletion of HIF-1' gene in T cells has been confirmed in control experiments.

To determine whether HIF-1α in T cells does indeed inhibit them during sepsis, we performed cecal ligation and puncture (CLP) on HIF-1α knockout mice and their HIF-1α expressing littermates. The data in FIG. 1a show that the selective deletion of HIF-1α in T cells results in dramatic increase in survival of mice. In controls, the sham CLP surgery did not result in any mouse mortality (data not shown). In agreement with observations of the improved survival, the HIF-1α gene deficient mice also had much less sepsis-associated tissue damage as demonstrated by a significant decrease in levels of liver enzymes (data not shown). Histological analysis of livers revealed many more apoptotic hepatocytes and fat accumulation in liver cells 72 hrs after CLP in HIF-1α-expressing lck Cre negative mice (not shown).

The described above protective effects of genetic inactivation of HIF-1α in T cells are most likely due to the relief from the negative regulation by HIF-1α of pro-inflammatory functions of T cells. This is supported by observations of dramatic inhibition of bacterial burden in spleen and liver of HIF-1α gene deficient mice as compared with HIF-1α expressing controls (FIG. 1B). The quantitative data on bacterial counts also revealed dramatic differences in the number of gas-forming bacteria that were observed in the spleen of HIF-1α-expressing mice, where masses of these bacteria formed rings around gas bubbles that also contained free bacteria (data not shown). Gas formation by bacteria usually indicates growth under anaerobic conditions revealing areas of severe hypoxia in some spleens at this stage of sepsis. Under these conditions T cells are expected to experience effects of hypoxia-induced stabilization of HIF-1α. In contrast to WT mice, such intensive bacterial growth was not observed in spleens of mice which do not express HIF-1α providing direct evidence that HIF-1α inhibits anti-bacterial activities of T cells.

Thus, the HIF-1α deficiency in T cells rescues mice from septic death and bacteria-mediated tissue damage (FIG. 1) and this is most likely explained by "de-inhibition" of pro-inflammatory cytokines secretion by TCR activated T cells. The ability of HIF-1α to inhibit T cells functions is also supported by other in vitro experiments with control and HIF-1α gene deficient T cell lines independently obtained from chimeric mice where HIF-1α was genetically inactivated using RAG-2 gene complementation system and by ex vivo experiments with cells from mice which have selective deletion of HIF-1α in their T cells. Comparison of TCR-triggered IFN-γ secretion in HIF-1α deficient T cell line vs. control HIF-1□ expressing T cell line revealed higher IFN-γ production in HIF-1α-deficient T cells in measurements of extracellularly secreted IFN-γ (Data not shown) or by increased percentages of cells staining positive for this cytokine. More detailed analysis of extracellularly secreted cytokine profiles showed also significantly higher production of other cytokines such as TNF-α and IL-2 by HIF-1α-deficient T-cell line as compared with the HIF-1α expressing T cell line upon T-cell receptor stimulation alone or costimulation with anti-CD28 antibody.

When peritoneal or splenic T cells recovered 72 h after CLP were restimulated ex vivo with anti TCR antibody, fluorescence intensity of intracellular staining for IFN-γ in T cells was higher in HIF-1α gene deficient mice than in WT mice. In agreement with INF-γ acting as an autocrine or paracrine biological immune response modifier which enhances the production of other pro-inflammatory cytokines, levels of TNF-α, MIP-2, IL-6 were higher in blood serum and peritoneal lavage fluid in HIF-1α gene deficient mice than in control WT mice after cecal ligation and puncture (Data not shown). Levels of the anti-inflammatory cytokine IL-10 were also significantly higher in HIF-1α knockout mice than in WT mice. Thus, the relief from HIF-1α mediated inhibition of production of pathogen-destroying cytokines may explain the observation of increased survival of mice with HIF-1α deficiency in T cells, since the complex interplay between pro-inflammatory and anti-inflammatory cytokines is known to play an important role in determining the degree of bacterial clearance and tissue damage. Accordingly, mice with selective disruption of HIF-1α gene in T-cells showed higher initial pro-inflammatory cytokine production followed by a stronger compensatory anti-inflammatory IL-10 response than control WT mice. This may explain the better bacterial clearance and improved survival.

Taken together, these observations suggest stronger inflammatory cytokine responses and anti-bacterial phagocyte effector mechanisms by de-inhibition of T-cell functions through selective disruption of the HIF-1α gene.

Yet another important implication of these studies is the inhibition of T cells in an opposite application, by using bioactive agents that stabilize HIF-1α protein expression in order to prevent autoimmune damage.

Example 1

FIG. 1A

This example demonstrates the ability of the present inventive method to modulate inflammation, cure bacterial sepsis and protect animals from septic death.

Survival studies reveal that mice with T cell lineage specific deletion of HIF-1α gene are more resistant to septic death initiated by lethal cecal ligation and puncture (CLP). Mice underwent CLP and were observed for mortality.

To determine if HIF-1α in T cells plays a role in septic infections, cecal ligation and puncture were performed on lck-Cre+HIF-1α fl+/fl+ mice (with specific deletion of HIF-1α only in T cells), and their HIF-1 expressing Cre+ littermates. It is shown that only 4 of 13 HIF-1 expressing mice survive the procedure, while 9 of 13 of the lck-Cre+ HIF-1α fl+/fl+ mice survive the procedure. Sham CLP surgeries did not result in mouse mortality (data not shown). This result is representative of several experiments Example 2

FIG. 1B

This example demonstrates the ability of the present inventive method to modulate inflammation and clear bacterial infection.

Mice with T cell selective deletion of HIF-1α gene are much more efficient in clearing bacterial infections.

The experiment similar to described above, except the bacterial burden was determined by routine methods.

Example 3

FIG. 1C

This example demonstrates the ability of the present inventive method to modulate inflammation and increase production of the cytokine IFN-γ by T cells.

HIF-1α is a negative regulator of cytokine production by activated in vivo T cells.

More IFN-γ is produced by HIF-1α-deficient T cells (dotted line) in vivo in acutely inflamed peritoneum, than in peritoneum of control mice with HIF-1α-expressing T cells.

Example 4

FIG. 2

This example demonstrates the ability of the present inventive method to modulate inflammation and increase production of the cytokine IFN-γ by T cells.

Example shows strong increase in IFN-γ secretion by T cells in vivo due to targeted deletion of HIF-1α gene in T cells. Lymph nodes lymphocytes from mice with T cell-specific deletion of HIF-1α (lck-cre+) were compared with lymphocytes from HIF-1α-expressing (lck-cre−) mice after 96 hr activation with anti-CD3/CD28 mAb (96 hrs). After the 2 days rest cells were re-stimulated 48 hrs anti-CD3/CD28 Ab again for 6 hrs (last 5 hrs with monensin) to facilitate detection of cytokines by flow cytometry after fixation and staining to detect IFN-γ in CD4 vs CD8+ T cells.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method to increase cell mediated immunity by increasing T-cell activity in a subject in response to a pathogen, comprising the step of administering an effective amount of at least one HIF-1α-affecting compound to the subject under conditions suitable for inducing said increase in said T-cell activity wherein said HIF-1α-affecting compound is a compound which interferes with HIF-1α gene expression and wherein the compound which interferes with HIF-1α gene expression is a nucleic acid or a nucleic acid analog that destroys the HIF-1α gene or that inhibits HIF-1α gene mRNA expression.

2. The method of claim 1, wherein the subject in need is selected from the group consisting of:
a patient having an infectious disease selected from the group consisting of: a bacterial infection or a viral infection.

3. The method of claim 2, wherein the infectious disease is selected from the group consisting of sepsis, septic shock, encephalitis, infectious arthritis, endotoxic shock, gram negative shock, Jarisch-Herxheimer reaction, shingles, chicken pox, small pox, toxic shock, cerebral malaria, bacterial meningitis, acute respiratory distress syndrome (ARDS), severe acute respiratory syndrome (SARS), tuberculosis (TB), lyme disease, HIV infection, TNF-α-enhanced HIV replication, a mycoplasma infection, a parasitic infection, an opportunistic infection, a pneumocystis infection, a cytomegalovirus infection, a herpes virus infection, a mycobacterium infection, or a human immunodeficiency virus infection and TNF-α inhibition of reverse transcriptase inhibitor activity.

4. The method of claim 1 wherein the compounds that inhibit HIF-1α gene mRNA expression are small interfering RNA (siRNA) or ribozymes.

5. The method of claim 1 further comprising administering at least one anti-inflammatory drug.

6. The method of claim 5 wherein the at least one anti-inflammatory drug is selected from the group consisting of agonists of A2A adenosine receptors and agonists of A2B adenosine receptors.

7. The method of claim 5, wherein the administering of the at least one anti-inflammatory drug is before, after or simultaneous with the administration of the HIFα-affecting compound.

8. The method of claim 1 wherein the HIF-1α-affecting compound is administered in the form of a composition comprising said HIF-1α-affecting compound and at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,718,624 B2 | Page 1 of 1 |
| APPLICATION NO. | : 11/215224 | |
| DATED | : May 18, 2010 | |
| INVENTOR(S) | : Sitkovsky | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 115 days.

Signed and Sealed this
Fourth Day of October, 2011

David J. Kappos
*Director of the United States Patent and Trademark Office*